(12) United States Patent
Swaim et al.

(10) Patent No.: US 7,595,169 B2
(45) Date of Patent: Sep. 29, 2009

(54) METHOD FOR DETERMINING PERCENT PLATELET AGGREGATION

(75) Inventors: Lisa Swaim, Carlsbad, CA (US); Dennis Durbin, Solana Beach, CA (US)

(73) Assignee: Accumetrics, Inc., San Diego, CA (US)

( * ) Notice: Subject to any disclaimer, the term of this patent is extended or adjusted under 35 U.S.C. 154(b) by 388 days.

(21) Appl. No.: 11/411,239

(22) Filed: Apr. 24, 2006

(65) Prior Publication Data

US 2006/0246528 A1 Nov. 2, 2006

Related U.S. Application Data

(60) Provisional application No. 60/675,513, filed on Apr. 27, 2005.

(51) Int. Cl.
*C12Q 1/56* (2006.01)
(52) U.S. Cl. .......................................... 435/13; 422/73
(58) Field of Classification Search ........................ None
See application file for complete search history.

(56) References Cited

U.S. PATENT DOCUMENTS

| | | | |
|---|---|---|---|
| 3,518,057 A | 6/1970 | Giordano | |
| 3,694,161 A | 9/1972 | Kleszynski et al. | ........ 23/230 B |
| 4,051,236 A | 9/1977 | Harris et al. | |
| 4,066,360 A | 1/1978 | Breddin | ........................ 356/39 |
| 4,820,836 A | 4/1989 | Mori et al. | |
| 5,023,233 A | 6/1991 | Nutt et al. | |
| 5,066,592 A | 11/1991 | Huang et al. | |
| 5,242,810 A | 9/1993 | Maraganore et al. | |
| 5,763,199 A | 6/1998 | Coller | |
| 5,922,551 A | 7/1999 | Durbin et al. | |
| 6,016,712 A * | 1/2000 | Warden et al. | ........... 73/864.21 |
| 6,043,871 A | 3/2000 | Solen et al. | |
| 6,063,847 A | 5/2000 | Chackalamannil et al. | |
| 6,210,904 B1 | 4/2001 | Bednar et al. | |
| 6,326,380 B1 | 12/2001 | Chackalamannil et al. | |
| 6,555,064 B2 | 4/2003 | Baugh et al. | ................ 422/68.1 |
| 6,589,992 B2 * | 7/2003 | Uckun | ......................... 514/626 |
| 6,645,987 B2 | 11/2003 | Chackalamannil et al. | |
| 6,894,065 B2 | 5/2005 | Chackalamannil et al. | |
| 7,037,920 B2 | 5/2006 | Chackalamannil et al. | |
| 7,244,730 B2 | 7/2007 | Suzuki et al. | |
| 7,304,083 B2 | 12/2007 | Suzuki et al. | |
| 2005/0031616 A1 | 2/2005 | Coller et al. | |
| 2006/0246528 A1 | 11/2006 | Swaim et al. | |
| 2007/0243632 A1 | 10/2007 | Coller et al. | |

FOREIGN PATENT DOCUMENTS

| WO | WO-2000-25140 | 5/2000 |
|---|---|---|
| WO | WO-2004/036226 | 4/2004 |
| WO | WO-2005/007868 | 1/2005 |

OTHER PUBLICATIONS

Ahn et al., Bioorg. Med. Chem. Lett. (1999) 9:2073-2078.
Angiolillo et al., "Functional Effects of High Clopidogrel Maintenance Dosing in Patients with Inadequate Platelet Inhibition on Standard Dose Treatment," The American Journal of Cardiology Online (Dec. 17, 2007) DOI: 10.1016/j.amjcard.2007.09.087.
Beer et al:, Blood (1992) 79(1):117-128.
Behan et al., Platelets (2005) 16(2):73-80 (abstract only).
Bernatowicz et al., J. Med. Chem. (1996) 39:4879-4887.
Chibata, "Immobilized Enzymes", Halsted Press, New York, 1978 [work reviewed by T.M.S. Chang, Quarterly Rev Biol (1979) 54(3):321].
Coller et al., J. Clin. Invest. (1983) 72:325-338.
Cook et al., Drugs of the Future (1994) 19:135-159.
Coughlin, PNAS USA (1999) 96:11023-11027.
Covic et al., Biochemistry (2000) 39:5458-5467.
Covic et al., Thromb. Haemost. (2002) 87:722-727.
Cuatrecasas, J. Biol. Chem. (1970) 245:3059-3065.
The Epic Investigators, N.E. J. Med. (1994) 330:956-961.
Fox et al., Cell Calcium (2004) 35:39-46.
Gurbel et al., Journal of the American College of Cardiology (2007) 50(19):1822-1834.
Hoekstra et al., Bioorg. Med. Chem. Lett. (1998) 8:1649-1654.
Hung et al., J. Biol. Chem. (1992) 267:20831-20834.
Hung et al., J. Clin. Invest. (1992) 89:1350-1353.
International Search Report for PCT/US04/21785, mailed on Jun. 13, 2005, 4 pages.
Kahn et al., J. Clin. Invest. (1999) 103:879-887.
Kahn et al., Nature (1998) 394:690-694.
Kay et al., Stroke (2007) 38(12):3259-3265.
Kim et al., Circ. J. (2007) 71:1867-1872.
Kogushi et al., J. Thromb. Haemost. (2007) 5(Suppl. 1):P-M-059.
MacFarlane et al., Pharmacol. Rev. (2001) 53:245-282.
Maryanoff et al., Curr. Med. Chem. Cardiovasc. Hematol. Agents (2003) 1(1):13-36.
McLean and Cannon, Critical Pathways in Cardiology (2006) 5:103-113.
McLean and Cannon, Future Cardiol. (2006) 2:255-267.
McComsey et al., Bioorg. Med. Chem. Lett. (1999) 9:255-260.
Muller et al., Thrombosis and Haemostasis (2003) 89(5):783-787.
O'Donnell et al., Stroke (2008) 39:1638-1646 (published online before print on Mar. 27, 2008).

(Continued)

*Primary Examiner*—Ralph Gitomer
(74) *Attorney, Agent, or Firm*—Morrison & Foerster LLP

(57) ABSTRACT

A method for obtaining a percent aggregation or inhibition of platelets resulting from anti-platelet using a single blood sample is achieved. An assay device is provided. The assay device has multiple channels, each coupled to a common introduction port. A first platelet activator is sensitive to activation pathway targeted by the anti-platelet drug. A second platelet activator is insensitive to the activation pathway targeted by the anti-platelet drug. An anti-coagulated sample is introduced simultaneously to the first and second channels. A level of platelet aggregation is simultaneously made in both channels.

5 Claims, 1 Drawing Sheet

OTHER PUBLICATIONS

Savi and Herbert, Seminars in Thrombosis and Hemostasis (2005) 31:174-183.
Soslau et al., J. Biol. Chem. (2001) 276(24):21173-21183.
Storey et al., Thromb. Haemost. (2002) 88(3):488-494.
Storey et al., Thromb. Res. (2005) 115(4):301-307.
Vassallo et al., J. Biol. Chem. (1992) 267:6081-6085.
Vu et al., Cell (1991) 64:1057-1068.
Vu et al., Nature (1991) 353:674-677.
Written Opinion of the International Searching Authority for PCT/US04/21785, mailed on Jun. 13, 2005, 4 pages.
Xu et al., PNAS USA (1998) 95:6642-6646.
U.S. Appl. No. 10/886,155, filed on Jul. 6, 2004.
Restriction Requirement for U.S. Appl. No. 10/886,155, mailed on May 17, 2005.
Response to Restriction Requirement for U.S. Appl. No. 10/886,155, filed on Jun. 22, 2005.
Response to Restriction Requirement for U.S. Appl. No. 10/886,155, filed on Jul. 11, 2005.
Non-Final Office Action for U.S. Appl. No. 10/886,155, mailed on Aug. 1, 2005.
Response to Office Action for U.S. Appl. No. 10/886,155, filed on Dec. 27, 2005.
Notice of Non-Compliant Amendment for U.S. Appl. No. 10/886,155, mailed on Feb. 9, 2006.
Response to Office Action for U.S. Appl. No. 10/886,155, filed on Feb. 15, 2006.
Final Office Action for U.S. Appl. No. 10/886,155, mailed on Mar. 7, 2006.
Request for Continued Examination and Response to Office Action for U.S. Appl. No. 10/886,155, filed on Sep. 7, 2006.
Non-Final Office Action for U.S. Appl. No. 10/886,155, mailed on Oct. 26, 2006.
Response to Office Action for U.S. Appl. No. 10/886,155, filed on Apr. 25, 2007.
Final Office Action for U.S. Appl. No. 10/886,155, mailed on Jul. 9, 2007.
Final Office Action for U.S. Appl. No. 10/886,155, mailed on Aug. 8, 2007.
Request for Continued Examination and Amendment After Final Action for U.S. Appl. No. 10/886,155, filed on Jan. 7, 2008.
Interview Summary for U.S. Appl. No. 10/886,155, mailed on Jan. 31, 2008.
Statement of Substance of Interview for U.S. Appl. No. 10/886,155, filed on Feb. 20, 2008.
Restriction Requirement for U.S. Appl. No. 10/886,155, mailed on Mar. 19, 2008.
Response to Restriction Requirement for U.S. Appl. No. 10/886,155, filed on Apr. 18, 2008.
U.S. Appl. No. 11/742,684, filed on May 1, 2007.
U.S. Appl. No. 12/114,498, filed on May 2, 2008.
Database Medline, database accession No. NLM11285593 (2001).
Supplementary European Search Report for EP 06769917.3, mailed Jul. 9, 2008, 8 pages.

* cited by examiner

*PRIOR ART*

METHOD FOR DETERMINING PERCENT PLATELET AGGREGATION

CROSS-REFERENCE TO RELATED APPLICATIONS

This application claims the benefit of U.S. Ser. No. 60/675,513, filed Apr. 27, 2005, which application is fully incorporated herein by reference.

BACKGROUND OF THE INVENTION

1. Field of the Invention

This invention relates generally to methods and devices for determining the percent inhibition of platelets, and more particularly to methods and devices for determining the percent inhibition of platelets when treated with drugs that suppress various activation pathways of platelets.

2. Description of the Related Art

The role of platelets in mammalian physiology is extraordinarily diverse, but their primary role is in promoting hemostasis. In many situations, an evaluation of the ability of blood to clot is desired, a parameter that is frequently controlled by the ability of platelets to adhere and/or aggregate. Of interest, therefore, is the assessment of the adhesive functions of platelets. For example, questions of interest include whether to administer drugs that will block, or promote, clot formation, or whether to detect deficiencies in platelet function prior to surgical procedures. Also of interest is evaluating the effectiveness of a platelet inhibitor that is being tested as a new drug or is being used as approved clinical treatment in a patient.

Platelets play a critical role in the maintenance of normal hemostasis. When exposed to a damaged blood vessel, platelets will adhere to exposed sub-endothelial matrix. Following the initial adhesion, various factors released or produced at the site of injury such as thrombin, ADP and collagen activate the platelets. Once platelets are activated, a conformational change occurs in the platelet glycoprotein GPIIb/IIIa receptor, allowing it to bind fibrinogen and/or von Willebrand factor. It is this binding of the multivalent fibrinogen and/or von Willebrand factor molecules by GPIIb/IIIa receptors on adjacent platelets that results in the recruitment of additional platelets to the site of injury and their aggregation to form a hemostatic plug or thrombus.

Platelet aggregation is a term used to describe the binding of platelets to one another. In vitro platelet aggregometry is the laboratory method used to assess the in vivo ability of platelets to form the aggregates leading to a primary hemostatic plug. In this technique an anti-coagulated whole blood sample is centrifuged under multiple conditions to create both a platelet-rich plasma (PRP) and platelet-poor plasma (PPP) sample. An aggregating agent such as ADP or collagen is then added to the PRP and aggregation of platelets monitored optically while in parallel with this, a separate optical measurement is made using the PPP sample. The percent aggregation is then determined by use of the PPP channel as the 100% aggregation reference level to compare with the PRP channel. Because the centrifugation of the blood can result in hemolysis of the red-blood cells, the change in optical density of the PPP due to preparation variability can result in errors in the optical reference level used to calculate the percent aggregation.

Another in vitro platelet aggregometry method used in the laboratory to assess in vivo platelet aggregation capability, uses diluted whole blood to measure the change in electrical impedance between two closely spaced precious metal electrodes as platelets adhere and aggregate after addition of an aggregating agent such as ADP, or collagen. With this method, there is no single assay means to determine the percent of platelet aggregation. Instead, two separate assays must be run and the ratio between the two measurements taken to determine the percent aggregation. For the case where the patient is already on a platelet inhibiting drug, there is no means of determining their percent of platelet aggregation. Current assays to measure platelet aggregation are expensive, time-consuming, cumbersome, and generally not suitable for a clinical environment.

A rapid platelet function assay has recently been developed and is described in U.S. Pat. No. 5,763,199. The assay determines glycoprotein (GP)IIb/IIIa receptor blockade in undiluted whole blood. Agglutination of small polymeric beads coated with a GPIIb/IIIa ligand such as fibrinogen results when the beads are contacted with whole blood containing platelets with activated GPIIb/IIIa receptors that are not blocked. Failure to agglutinate indicates either failure of the GPIIb/IIIa receptors to become activated and/or blockade of the GPIIb/IIIa receptors. In a preferred embodiment, the addition of a platelet activator like ADP or arachidonic acid, results in an assay that is rapid and convenient enough to be performed at the bedside and that results in agglutination of the small polymeric beads within a convenient, known period of time if the activation receptors are not blocked. The assay includes the ability to transfer blood to be tested from a collection container to an assay device without opening the collection container.

Platelet aggregation plays a key role in the pathogenesis of thrombosis and acute coronary artery disease. Evidence suggests that significant platelet function variability exists in the response to various antiplatelet agents. It has also been demonstrated that an inter-individual variability in platelet aggregation exists when P2Y12 antagonists such as clopidogrel are used for treatment of patients to achieve an anti-aggregation effect. The results of one study demonstrated that at least 10% of patients receiving the drug did not achieve the expected platelet aggregation inhibition (Muller I, Besta F, Schulz C, Massberg S, Schonig A, Gawaz M; Prevalence of clopidogrel non-responders among patients with stable angina pectoris scheduled for elective coronary stent placemen Thromb Haemost. 2003 May, 89(5):783-7).

Since many patients with cardiovascular disease are chronically taking one of the thienopyridine agents, a method for determining the level of platelet inhibition based on a single measurement of an inhibited sample would be beneficial. In addition, patients undergoing PTCA procedures are generally given a large bolus dose of a thienopyridine agent prior to the procedure. Some of these patients may then require emergent surgery and an assay that would provide information about their absolute level of platelet inhibition would be beneficial in assessing the bleeding management risks prior to surgery.

There is a need for an improved method for obtaining a percent aggregation or inhibition of platelets, due to anti-platelet drugs. There is a further need for a method for obtaining a percent aggregation or inhibition of platelets, due to anti-platelet drugs, using a single blood sample. There is yet a further need for a method for obtaining a percent aggregation or inhibition of platelets, due to anti-platelet drugs, in a single measurement.

SUMMARY OF THE INVENTION

Accordingly, an object of the present invention is to provide an improved method for determining a percent aggregation or inhibition of platelets, due to anti-platelet drugs.

Another object of the present invention is to provide a method for obtaining a percent aggregation or inhibition of platelets, due to anti-platelet drugs, using a single blood sample.

Yet another object of the present invention is to provide a method for obtaining a percent aggregation or inhibition of platelets, due to anti-platelet drugs, in a single measurement.

These and other objects of the present invention are achieved in a method for obtaining a percent aggregation or inhibition of platelets, resulting from anti-platelet drugs including but not limited to, aspirin, thienopyridine, cilostazol, and the like using a single blood sample. An assay device is provided. The assay device has multiple channels, each coupled to a common introduction port. A first platelet activator is introduced to a first channel of the assay device. The first platelet activator is sensitive to an activation pathway targeted by the anti-platelet drug. A second platelet activator is introduced to a second channel of the assay device. The second platelet activator is insensitive to the activation pathway targeted by the anti-platelet drug. An anti-coagulated sample is introduced simultaneously to the first and second channels. A level of platelet aggregation is simultaneously made in both channels. By way of illustration, and without limitation, the level of platelet aggregation can be determined by an optical turbidimetric method. The percent or platelet aggregation (PA) or inhibition (PI) is determined as follows:

% PA=(Test Channel/Control Channel)*100%
% PI=(1−(Test Channel/Control Channel))*100%=100%−% PA

DESCRIPTION OF THE PREFERRED EMBODIMENTS

Figure 1:
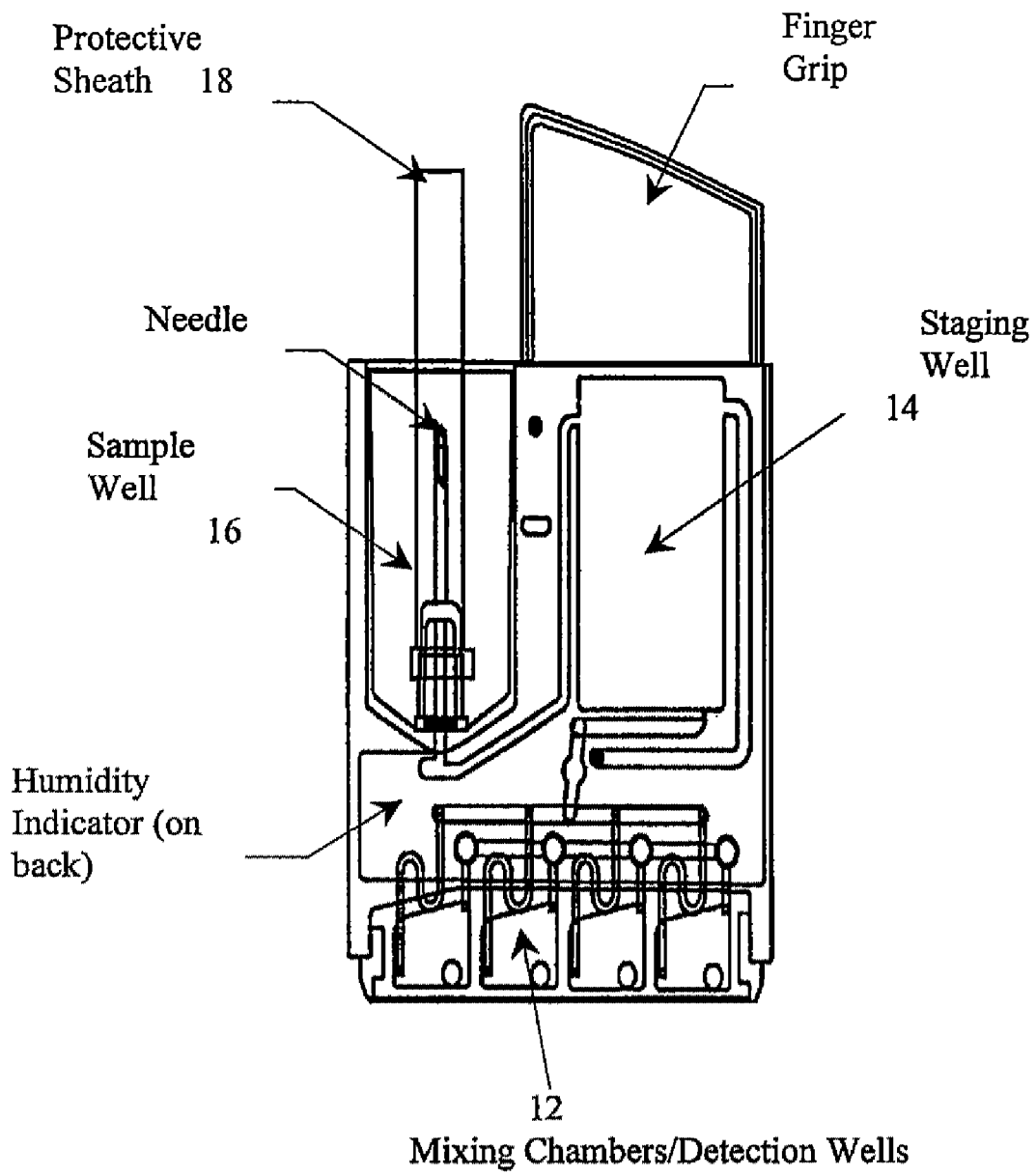
FIG. 1 is a diagram of an assay device that can be used with the present invention, with a plurality of mixing chambers/detection wells, a staging well, a sample well and a protective sheath.

In one embodiment of the present invention, a percent aggregation or inhibition of platelets, due to anti-platelet drugs, is determined using a single blood sample. As illustrated in FIG. 1, an assay device, generally denoted as 10 is provided. The assay device 10 includes a plurality of mixing chambers/detection wells 12, a staging well 14, a sample well 16 and a protective sheath 18. Assay device is used for independent and simultaneous assays of the blood sample. A cartridge is provided.

The cartridge has multiple channels, each coupled to a common introduction port. A first platelet activator is introduced into a first channel. The first platelet activator is sensitive to an activation pathway targeted by the anti-platelet drug. Suitable first platelet activators include but are not limited to, arachidonic acid, ADP, collagen, thromboxane A2, epinephrine and the like. A second platelet activator is introduced into a second channel of the cartridge. The second platelet activator is insensitive to the activation pathway targeted by the anti-platelet drug. Suitable second platelet activators include but are not limited to, thrombin, iso-TRAP and the like.

An anti-coagulated sample is introduced simultaneously to the first and second channels. A level of platelet aggregation is simultaneously made in both channels. By way of illustration, and without limitation, the level of platelet aggregation can be determined by an optical turbidimetric method.

A percent or platelet aggregation (PA) or inhibition (PI) is as follows:

% PA=(Test Channel/Control Channel)*100%
% PI=(1−(Test Channel/Control Channel))*100%=100%−% PA The comparison is made in the assay device 10.

In one specific embodiment, the assay device 10 is an instrument that measures a change in optical signal due to agglutination. Suitable instruments include, by way of illustration and not limitation a kinetic spectrophotometer, Ultegra System® instrument (commercially available from Accumetrics, San Diego, Calif.) and employed for rapid platelet function activity measurements on normal samples), and the like.

The Ultegra® System instrument is a turbidometric based optical detection system, that measures platelet induced aggregation as an increase in light transmittance. The system consists of an analyzer, disposable cartridge and controls. The cartridge contains reagents based on microparticle agglutination technology. The quality control system includes an electronic control, two levels of assayed "wet" controls (WQC), an in-cartridge humidity sensor, an in-packaging temperature indicator, and a test for concurrence of two assay channels. The analyzer controls assay sequencing, establishes the assay temperature, controls the reagent-sample mixing for the required duration, determines the degree of platelet function, displays the result and performs self-diagnostics.

In one specific embodiment of the present invention, the cartridge includes a lyophilized preparation comprising particles with covalently attached GPIIb/IIIa receptor ligand, a composition of AA and ascorbic acid, and buffer. The patient sample can be citrated whole blood, which is automatically dispensed from a blood collection tube into the cartridge by the analyzer, with no blood handling required by the user. The interaction is monitored by the infrared absorbency characteristics of the particles. As the particles interact with the platelets, the agglutination of the particles is measured through the optical system of the Ultegra™ analyzer. The agglutination is detected as an increase in the transmission of infrared light through the sample. The reaction kinetics are analyzed and translated into "Aspirin Response Units", ARU.

Isolated reagents are in the individual channels of the cartridge. However, there is a common introduction of the sample into both channels. The assay device 10 controls the introduction of the blood sample, the mixing of the reagent with the blood sample, the independent optical measurement of aggregation for each active channel, and the determination of the % PI based upon the individual channel results.

The present invention provides a single assay to determine the level of platelet inhibition relative to a patient's uninhibited level even when a patient with drug induced platelet inhibition is measured.

EXAMPLE 1

Blood Assay for Determining Blockade of Platelet Receptors

Blood is drawn from a patient by syringe and placed in a standard blue-top tube containing sodium citrate (1 volume of 3.8% sodium citrate). Alternatively, blood may be drawn by vacutainer directly into a blue-top tube.

The tube is then inverted to mix the anticoagulant with the whole blood. Then 50 .mu.l of this mixture is added to 50 .mu.l of buffer (0.15M NaCl, 5 mM CaCl.sub.2, 0.05M HEPES, pH 7.4) and to 5 .mu.l. An anti-coagulated sample is introduced simultaneously to the first and second channels of the cartridge.

If GPIIb/IIIa receptors are blocked, the beads remain in suspension. If the GPIIb/IIIa receptors are not blocked, the platelets interact with the fibrinogen bound to the surface of the beads, resulting in clumping of the beads. A level of platelet aggregation is simultaneously made in both channels by assay device 10.

EXAMPLE 2

Blood Assay for Determining Blockade of Platelet Receptors

Blood is drawn from a patient by syringe and placed in a standard blue-top tube containing sodium citrate (1 volume of 3.8% sodium citrate). Alternatively, blood may be drawn by vacutainer directly into a blue-top tube.

The blood sample is introduced in the first and second channels of the cartridge at the same time. The assay device 10 controls the introduction of the blood sample, the mixing of the reagent with the blood sample, the independent optical measurement of aggregation for each active channel, and the determination of the % PI based upon the individual channel results.

A first plate activator, arachidonic acid, is in the first channel. A second platelet activator, thrombin, is introduced into the second channel of the cartridge. A level of platelet aggregation is simultaneously made in both channels by assay device 10.

EXAMPLE 3

Blood is drawn from a patient by syringe and placed in a standard blue-top tube containing sodium citrate (1 volume of 3.8% sodium citrate). Alternatively, blood may be drawn by vacutainer directly into a blue-top tube.

The blood sample is introduced in the first and second channels of the cartridge at the same time. The assay device 10 controls the introduction of the blood sample, the mixing of the reagent with the blood sample, the independent optical measurement of aggregation for each active channel, and the determination of the % PI based upon the individual channel results.

A first platelet activator, ADP, is in the first channel. A second platelet activator, iso-TRAP, is in the second channel. A level of platelet aggregation is simultaneously made in both channels by assay device 10.

EXAMPLE 4

Blood Assay for Determining Blockade of Platelet Receptors

Blood is drawn from a patient by syringe and placed in a standard blue-top tube containing sodium citrate (1 volume of 3.8% sodium citrate). Alternatively, blood may be drawn by vacutainer directly into a blue-top tube.

The blood sample is introduced in the first and second channels of the cartridge at the same time. The assay device 10 controls the introduction of the blood sample, the mixing of the reagent with the blood sample, the independent optical measurement of aggregation for each active channel, and the determination of the % PI based upon the individual channel results.

A first platelet activator, thromboxane A2, is in the first channel. A second platelet activator, thrombin, is in the second channel. A level of platelet aggregation is simultaneously made in both channels by assay device 10.

EXAMPLE 5

Blood Assay for Determining Blockade of Platelet Receptors

Blood is drawn from a patient by syringe and placed in a standard blue-top tube containing sodium citrate (1 volume of 3.8% sodium citrate). Alternatively, blood may be drawn by vacutainer directly into a blue-top tube.

The blood sample is introduced in the first and second channels of the cartridge at the same time. The assay device 10 controls the introduction of the blood sample, the mixing of the reagent with the blood sample, the independent optical measurement of aggregation for each active channel, and the determination of the % PI based upon the individual channel results.

A first platelet activator, epinephrine, is in the first channel. A second platelet activator, iso-TRAP, is in the second channel. A level of platelet aggregation is simultaneously made in both channels by assay device 10.

The foregoing description of embodiments of the invention have been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

The invention claimed is:

1. A method for obtaining a percent activation of aggregation or inhibition of aggregation of platelets in an anti-coagulated blood sample from an individual treated with an anti-platelet drug, comprising:
   (a) providing an assay device having a first channel (Test Channel) and a second channel (Control Channel);
   (b) introducing a first platelet activator to the first channel (Test Channel) of the assay device, the platelet activator being sensitive to an activation pathway targeted by the anti-platelet drug;
   (c) introducing a second platelet activator to the second channel (Control Channel) of the assay device, the second platelet activator being insensitive to the activation pathway targeted by the anti-platelet drug;
   (d) introducing the anti-coagulated blood sample to the assay device;
   (e) simultaneously measuring a level of platelet aggregation in both channels; and
   (f) determining a percent platelet aggregation (PA) or inhibition (PI) as follows:
   % PA=(Test Channel/Control Channel)*100%
   % PI=(1−(Test Channel/Control Channel))*100%=100%−% PA.

2. The method of claim 1, wherein the first platelet activator is selected from the group consisting of arachidonic acid, ADP, collagen, thromboxane A2 and epinephrine.

3. The method of claim 1, wherein the second platelet activator is selected from the group consisting of thrombin and iso-thrombin receptor-activating peptide (iso-TRAP).

4. The method of claim 1, wherein the anti-coagulated sample is selected from the group consisting of undiluted whole blood, plasma and diluted whole blood.

5. The method of any of the preceding claims, wherein the anti-platelet drug is clopidogrel.

* * * * *

UNITED STATES PATENT AND TRADEMARK OFFICE
CERTIFICATE OF CORRECTION

PATENT NO. : 7,595,169 B2
APPLICATION NO. : 11/411239
DATED : September 29, 2009
INVENTOR(S) : Swaim et al.

Page 1 of 1

It is certified that error appears in the above-identified patent and that said Letters Patent is hereby corrected as shown below:

IN THE SPECIFICATION:

At column 5, line 2, ".mu.l" should read --µl--.

At column 5, line 3, ".mu.l" should read --µl--.

At column 5, line 3, "CaCl.sub.2." should read --$CaCl_2$--.

At column 5, line 4, ".mu.l" should read --µl--.

At column 5, line 29, "plate activator" should read --platelet activator--.

Signed and Sealed this

Twenty-ninth Day of December, 2009

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,595,169 B2 | Page 1 of 1 |
| APPLICATION NO. | : 11/411239 | |
| DATED | : September 29, 2009 | |
| INVENTOR(S) | : Swaim et al. | |

It is certified that error appears in the above-identified patent and that said Letters Patent is hereby corrected as shown below:

On the Title page,

[*] Notice:    Subject to any disclaimer, the term of this patent is extended or adjusted under 35 USC 154(b) by 388 days Delete the phrase "by 388 days" and insert -- by 529 days --

Signed and Sealed this

Eighteenth Day of May, 2010

David J. Kappos
*Director of the United States Patent and Trademark Office*